United States Patent
Wang

(10) Patent No.: US 6,537,229 B1
(45) Date of Patent: Mar. 25, 2003

(54) METHOD AND APPARATUS FOR MONITORING AND IMPROVING BLOOD CIRCULATION BY RESONANCE

(76) Inventor: Wei-Kung Wang, No. 14, Sublane 3, Lane 61, Sec. 2, Yen Chiu Yuan Rd., Nan Kang District, Taipei (TW)

( * ) Notice: Subject to any disclaimer, the term of this patent is extended or adjusted under 35 U.S.C. 154(b) by 189 days.

(21) Appl. No.: 09/604,087

(22) Filed: Jun. 27, 2000

(51) Int. Cl.$^7$ ................. A61B 5/02; A61B 5/00

(52) U.S. Cl. ............. 600/508; 600/300; 600/504; 607/2; 607/3; 607/61

(58) Field of Search ............ 600/38–41, 9–15, 600/300, 504, 508, 481, 500; 607/1, 2, 4, 5, 7, 9, 10, 11, 12, 33, 37, 44, 61, 100, 101, 103, 115, 50; 623/3.1, 3.11, 3.27

(56) References Cited

U.S. PATENT DOCUMENTS

| | | | | |
|---|---|---|---|---|
| 4,788,983 A | * | 12/1988 | Brink et al. | 600/519 |
| 5,125,890 A | * | 6/1992 | Merrill et al. | 600/39 |
| 5,346,458 A | * | 9/1994 | Affeld | 600/16 |
| 5,423,869 A | * | 6/1995 | Poore et al. | 607/18 |
| 5,814,078 A | * | 9/1998 | Zhou et al. | 607/1 |
| 6,013,096 A | * | 1/2000 | Tucek | 606/13 |
| 6,042,537 A | * | 3/2000 | Kaiser | 600/38 |
| 6,217,604 B1 | * | 4/2001 | Azure et al. | 600/14 |
| 6,221,021 B1 | * | 4/2001 | Redano | 600/454 |

FOREIGN PATENT DOCUMENTS

RO 365529 8/1999

OTHER PUBLICATIONS

Wang Lin Y. Y., Chang S. L., Wu Y. E., Hsu T. L. and Wang W. K., *Resonance: the missing phenomena in hemodynamics*, Circulation Research 1991, 69 pp. 246–249.

Yu G. L., Wang Lin Y. Y. and Wang W. K., *Resonance in the kidney system of rat*, Am J of Physiol. 1994, 267 H1544–1548.

Wang Lin Y. Y., Chang C. C., Chen J.C., Hsin H. and Wang W. K., *Pressure wave propagation in arteries—A model with radial dialation for simulation the behavior of a real artery*, IEEE Engineering in Med. & Biol. Jan./Feb. 1997, pp 51–56.

Wang W. K., Hsu Tse Lin, Chang H. C., Wang Lin Y. Y., *effect of acupunture at tsu san li (st–26) on the pulse spectrum*, Am. J. of Chin. Med. XXIII (2): pp. 121–130, 1995.

Wang W. K., Hsu Tse Lin, Huang Z. Y., Wang Lin Y. Y., collective *effect of a Chinese formula—a study of xiao–jian –zhong–tang*, Am. J. of Chin. Med. XXIII (3–4): pp. 299–304, 1995.

Wang W. K., Hsu Tse Lin, Chang H. C., Wang Lin Y. Y., *effect of acupuncture at hsien–ku (st–43) on the pulse spectrum and discussion of the evidence for the frequency structure of Chinese medicine*, Am. J. of Chin. Med. vol. 28 (1): pp. 41–55, 2000.

Wang Lin Y. Y., Lia W. C., Hsin Hsiu., Jan Ming–Yie, and Wang W. K., *effect of length on the fundamental resonance frequency of arterial models having radial dilatation*, IEEE 2000.

Wilmer W. Nichols, Michael F. O'Rourke, *McDonald's blood flow in arteries*, 4th ed. pp. 429–441, 1998.

\* cited by examiner

Primary Examiner—Max F. Hindenburg
Assistant Examiner—Navin Natnithithadha
(74) Attorney, Agent, or Firm—Senniger, Powers, Leavitt & Roedel

(57) ABSTRACT

The present invention relates to a method for improving the blood circulation of a human body by resonance, comprising the steps of: using an energy generating device to generate energy resonating with the body; and coupling the energy through a coupling device to the circulatory system of the body by functionally connecting the coupling device to the body and then activating the energy generating device.

38 Claims, 3 Drawing Sheets

METHOD AND APPARATUS FOR MONITORING AND IMPROVING BLOOD CIRCULATION BY RESONANCE

FIELD OF INVENTION

The present invention relates to a method and apparatus for monitoring the blood circulation in a human being by resonance.

BACKGROUND AND SUMMARY OF INVENTION

The artificial heart is a device that can supply energy to blood circulation. Its principle is to supply energy to the blood system to keep blood circulating. However, the circulatory system of a human body is a very complex system, and the blood is not circulating only by the momentum of the blood itself. In fact, the heart pumps the blood by squeezing it out of the left ventricle, and then, there is a U-turn at the ascending aorta, which converts the kinetic energy into elastic energy, stored on the arterial wall. If we measure the energy composition in the circulatory system, the result will be about 98% in the form of elastic energy in the aorta, and only 2% in the form of kinetic energy. Furthermore, more than half of the 2% kinetic energy is in oscillatory form and thus, only less than 1% of the total energy that keeps blood moving forward is in momentum form. Recently, the applicant has derived a formula of pressure wave propagation, which can explain the blood transfer in arteries and organs by pressure waves and resonance. Please view the following papers authored or co-authored by the applicant, as well as the references thereof:

1. Wang Lin Y. Y., Chang S. L., Wu Y. E., Hsu T. L. and Wang W. K., *Resonance: the missing phenomena in hemodynamics,* Circulation Research 1991, 69 pp. 246–249.
2. Yu G. L., Wang Lin Y. Y. and Wang W. K., *Resonance in the kidney system of rat,* Am J of Physiol. 1994, 267 H1544–1548.
3. Wang Lin Y. Y., Chang C. C., Chen J. C., Hsin H. and Wang W. K., *Pressure wave propagation in arteries—A model with radial dialatation for simulation the behavior of a real artery,* IEEE Engineering in Med. & Biol. January/February 1997, pp. 51–56.
4. Wang W. K., Hsu T. L., Chang H. C. and Wang Lin Y. Y., *Effect of acupuncture at Tai-Tsih (k3) on the pulse spectrum,* Am. J. of Chin. Med. VVIV (3–4): pp. 305–313, 1996.

The transfer of energy from the outside of a body toward the circulatory system inside the body can thus be understood in many different principles and can be realized in many different structures. One of the examples is the traditional artificial heart. However, the applied energy of the traditional artificial heart need not be momentum (i.e. kinetic), rather, it can also supply pressure energy (i.e. elastic) along with the blood flow. If the artificial device is a total artificial heart, it should pump the blood like the real heart that converts the blood flow momentum into elastic energy on the arterial wall. The artificial heart should be connected to the ascending aorta, and let the ascending aorta arch to do this conversion work. If the artificial device is in the form of a ventricular assistant device, especially the left ventricular assistant device, the energy applied by the device can be found everywhere. Along the artery, it is better for this applied energy to be in the form of pressure energy and synchronized with the heartbeat. For both the total artificial heart and the left ventricular assistant device, it is better to utilize the pulsatile energy delivering design which will excite the resonance of the host organs and the artery such that the impedance of blood circulation can be minimized.

The total artificial heart must be pulsatile at a beating rate that is similar to the beating rate of the heart to be replaced by the artificial one. Thus, a monitor is required for following the condition(s) of blood circulation. If the artificial heart is working properly, the pulse, which measures the resonant condition of the circulatory system, will show a pattern very close to the normal one. However, if a patient is dying, his or her heartbeat will generally become faster and body will begin swelling, due to edema. Then, the heartbeat will become abnormal or even irregular. If an artificial heart can perform its function at this time, the pulse will be normalized and the edema situation will improve, so that the heart rate can become slower and normal and the patient's heart failure is no longer fatal.

This monitoring system is very important because it gives instructions to tune the heartbeat. Among the many other ways to control blood circulation, the tuning of the heartbeat is the most useful way. One of the other ways is by monitoring the power in the delivered pulsatile pulse. In a normal human being, the power of the heart is only about 1.7 W. This limit should not be exceeded by much (e.g., the tradition artificial heart does not exceed 10 W). Too much pulsatile energy delivered may tune the whole circulatory system into another equilibrium state, which will damage internal organs in the long run. Again, the level of power should be made based on the monitoring of the pulse. When the pulse becomes normal, it implies the energy provided is sufficient. Therefore, the artificial heart should work within a small range of heartbeats and deliver energy by trial and error in order to seek an optimized heartbeat. Moreover, the delivered energy that produces the best pulse can be measured at the artery.

As a matter of fact, the above-mentioned principle explains the mechanism, as well as the reasons, for heart rate variability in a healthy heart. In a healthy heart, the feedback system on the arteries as well as the heart itself includes monitoring the blood distribution, and feed back of the monitored information through the nerve system to control the heartbeat and contractile force (if the heart is capable of following the instructions and delivering the requested power). If the artificial heart is requested to perform like a real heart, the monitoring system of the real heart, which is done by the artery and nerve system must be provided. Pulse analysis is of the simple and efficient ways to monitor artificially. Thus, an effective artificial heart is required to include both an energy delivering system and a monitoring system, in order to give feedback instructions concerning how the artificial heart should modify its rate and energy for optimized performance.

With respect to a ventricle assistant device, the real heart still works in the chest of the patient. Although the native feedback system works, the heart fails to deliver the requested power. Under this circumstance, the monitoring system should consult the native system constantly by way of monitoring the pulse together with the native heartbeat. Will the heart follow the changing of the beat and the delivered energy? Is the pulse getting closer to be normal? Two conditions should be followed. One is the pulse spectrum and the other is the native heart rate. A systematic way is to follow the pulse spectrum with heart rate variability. If the pulse is getting normal, the native heart rate variability becomes larger (and vice-versa, the variability becomes smaller when the native heart is working harder). A larger variability indicates that the conditions are fine.

Pulse monitoring should be used in both the total artificial heart and the left ventricle assistant device, and heart rate variability may also be used in the left ventricle device as an additional monitoring factor.

From the theory of resonance mentioned above, the heart beats an impulse which is converted into elastic energy on the arterial wall of the ascending aorta. The elastic energy is stored in the whole arterial system. It is comparable to an elastic bag in the body. The diastolic pressure inflates this bag, while the systolic pressure propagates along the arterial wall and distributes more energy into each organ and tissue. The blood is squeezed by this pressure and flows out of any holes in the arterial network. The blood flow in the artery is for refilling the arterial openings, from which blood leaks into the tissue.

Another way of helping the circulatory system is to supply more energy to the arterial wall, without penetration, by connecting a tube.

Energy may be supplied directly to the blood inside the artery by tapping the wall or rubbing the wall of the circulatory system.

Conventional devices for supplying energy to the circulatory system include electrical stimulators, massage apparatus, vibrators, foot massage apparatus, or vacuum enlargers (e.g. a suction cup), etc. All of these devices are designed to improve blood circulation by various kinds of stimuli. However, conventional devices do not improve blood circulation satisfactorily; and even worse, they have some drawbacks such as causing muscular twitch, or injury to the body. In general, the devices are short of useful monitoring mechanisms for detecting body conditions such that they cannot be appropriately adjusted or optimized and will cause the wasting of electrical energy.

Thus there is a need to provide an apparatus and method for efficiently monitoring and improving blood circulation. This invention addresses the need.

In one aspect of the invention, there is a method for monitoring resonant energy in the blood circulation of a human body, comprising the steps of: measuring the pressure wave formed in an artery of the body and producing an electrical pulse representing the blood pressure pulse; and calculating the amplitude and phase of harmonic components of the electrical pulse by applying the Fourier transformation to the electrical pulse resulting in the harmonics.

In another aspect of the invention, there is a method for improving the blood circulation of a human body by resonance, comprising the steps of: using an energy generating device to generate energy resonating with the body; and coupling the energy through a coupling device to the circulatory system of the body by functionally connecting the coupling to the body and then activating the energy generating device.

In a further aspect of the invention, there is a method for improving blood circulation of a human body, comprising playing music with a beat resonant with a designated meridian of the body by using a musical instrument with a meter synchronized with the heartbeat of the body, so that the body may dance or exercise accordingly.

By monitoring resonant energy in the blood circulation, through the Fourier transformation of the signals of the circulatory system, the invention provides a method for efficiently supplying energy to the circulatory system by resonance. Due to the resonance between the human body and the energy supplying device, the energy transferred will be constant and efficient causing no muscular twitch or injury to the body.

In yet another aspect of the invention, there is an apparatus for monitoring the blood circulation of a human body, comprising: (a) a light source for generating a light with a designated wave length; (b) a light guide for leading the generated light to a certain part of the body; and (c) a detector for measuring the change of intensity of the light; wherein, the measured intensity which represents the pressure wave form is converted to an electrical signal and sent to a signal processor for analyzing the Fourier transformation and coefficient of variance (C. V.) of the signal.

In yet another aspect of the invention, there is an apparatus for improving the blood circulation of a human body by resonance, comprising an energy generating device for generating an energy resonant with the body, and a coupling device for delivering the energy to the circulatory system of the body.

In yet another aspect of the invention, there is an apparatus for improving the blood circulation of a human body, comprising a musical instrument with a controllable meter to be synchronized with the heartbeat of the body, in order for the body to dance or exercise by playing music at a that is resonant with a designated meridian.

BRIEF DESCRIPTION OF DRAWINGS

The present invention now will become better understood with regard to the accompanying drawings in which.

DETAILED DESCRIPTION OF INVENTION

A preferred embodiment of the present invention will be now described below with reference to the accompanying drawings.

As mentioned before, the characteristics of the present invention for the transfer of energy in a circulatory system are mainly the matching of synchronization and impedance. There are two types of scale for the transfer of energy: one is on a global scale; and the other is on a local scale. On the global scale, the whole circulatory system of a human body is considered as one resonant unit (i.e. the inside unit) and, besides the circulatory system, those with similar wave length and frequency to those of the inside unit are considered another unit (e.g. the energy supplying system of an outside unit). When the outside unit is close to the inside unit. both units have the same resonance frequency and are synchronized. The resonance between the two units will help transfer energy from one unit (the outside unit) to the other (the inside unit). Such transferring can be measured in three scales by: I.) measuring the heart rate variability referred to as H.R.V.), because when the energy is transferred to the circulatory system, the H.R.V. will increase; II.) measuring the changing of the heart rate, because the native heartbeat can be driven by an outside unit within a small range; and III.) analyzing the pulse. The energy can thus be transmitted from the outside unit into the circulatory system. It is suggested that HRV and pulse analysis are good ways to monitor the efficiency of the transmission, and from the above-mentioned, the monitoring should be incorporated into the system in order to give feedback for controlling the transmitted energy.

Figure 1:
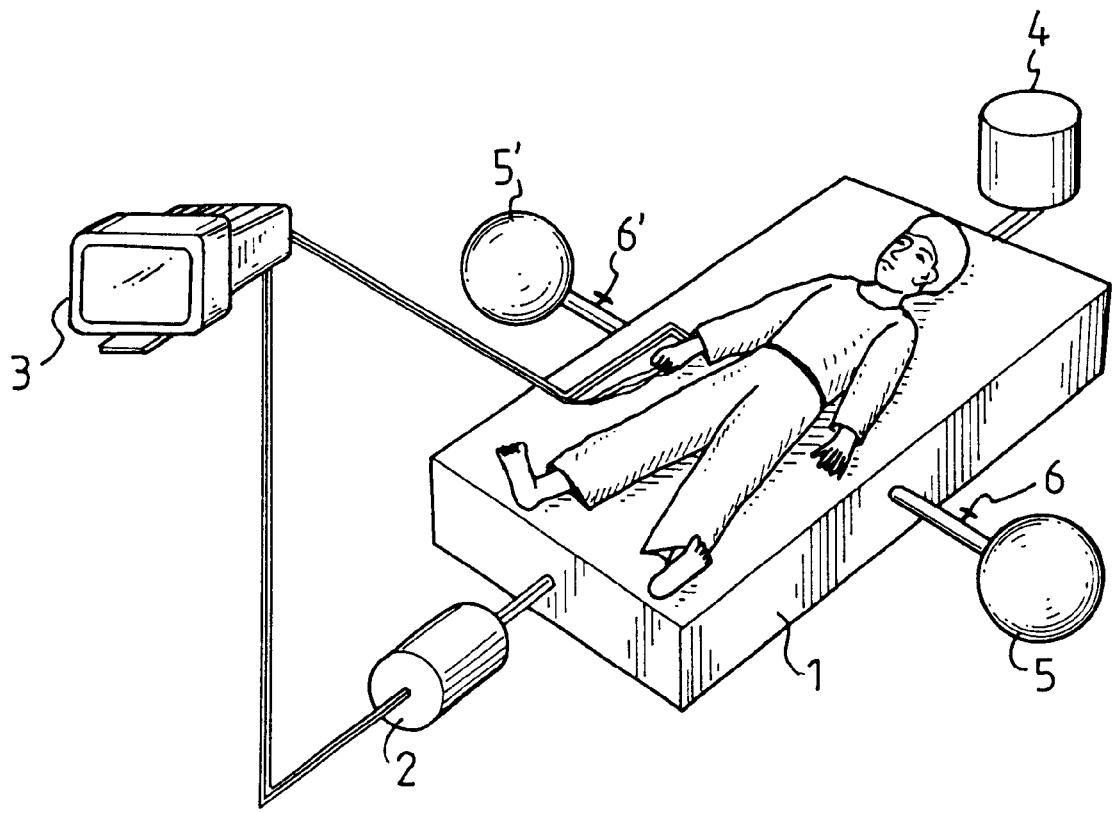
FIG. 1 shows an apparatus arrangement for monitoring and improving the blood circulation of a human body according to a preferred embodiment of the invention.

Please refer to FIG. 1. FIG. 1 shows a possible configuration of a preferred embodiment of a global scale transmission in the present invention. For a global scale transmission, the outside unit can be a bed (1) filled with liquid such as water. A vibration generator (2) is coupled to the bed (1), and a monitor (3) for HRV and pulse is connected to both the human body and the vibration generator. There is a pressure control device (4) for controlling the internal pressure of the bed (1), so that both the resonant frequency and the wave length of the water inside are the same as those of the circulatory system of the human body lying on the bed (1). Two outside units of resonant cavity (5 and 5'), along with two switches (6 and 6'), are arranged on both sides of the bed (1) and are in liquid conduction with each other. In other words, the frequency and the impedance are matched for both the inside and outside units. The outside units 5 and 5' are designed so as to fine-tune the resonance frequency.

In the case of transmitting energy on a global scale as shown in FIG. 1, the whole body is as one resonant unit. Therefore, the apparatus should be of similar size to that of the body. The apparatus can be in the form of a mattress on a bed to lie on, a chair to sit on, a back pack to carry, or a mat to stand on, and so forth. The resonant frequency of the apparatus can be controlled by the following factors: 1.) the construction material of the apparatus; 2.) the pressure of the apparatus; and 3.) the shape of the apparatus. To control the frequency, the internal pressure, as well as the shape, can be changed. As mentioned above, the resonant frequency (or frequencies) must be close to the patient's rate of heartbeat, or the harmonics of the rate of heartbeat. In this embodiment, the liquid inside the apparatus is of similar density to that of blood, so that a match in impedance can be achieved.

The energy is transmitted from the apparatus to the body, or more precisely, the circulatory system of the body. Since the heartbeat is at an energy level of about 1.7 W (for a human body weighing 75 Kg), the applied energy of the apparatus should be higher. The applied energy can be generated by beating the mattress at any spot. However, the anti-nodal point can be the most efficient spot for generating such energy by an outside beating device. The outside beating device could be a motor driven stick, a vibrator, etc. Once there is enough energy in the apparatus and the two units are closely contacted, the energy will be transmitted from the outside unit to the circulatory system by resonance.

The efficiency of the transmission can be monitored in two ways, one is HRV. If HRV increases, it means the energy is being transmitted to the body. If the pulse is changing towards normal, it means the energy is being transmitted efficiently. Therefore, the apparatus of this invention can achieve the similar effects to those of the artificial heart or the ventricle assistant device. However, the invention is much safer because no operation is involved. That means the transmission is a non-invasive one. Moreover, the mattress can be used as a sore preventing device and can improve blood circulation around a patient's wounded area. It can also improve blood circulation to any organ by tuning the resonance frequency to that of the organ.

Figure 2A:
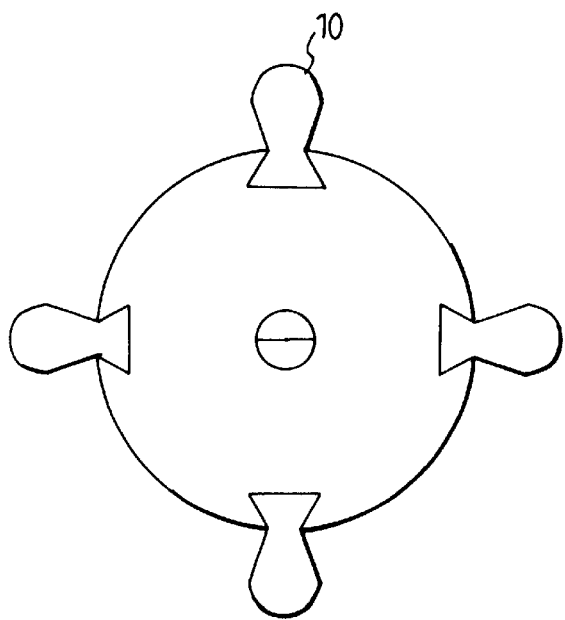
FIG. 2 shows an apparatus for improving the blood circulation of a human body according to another preferred embodiment of the invention.
Figure 2B:
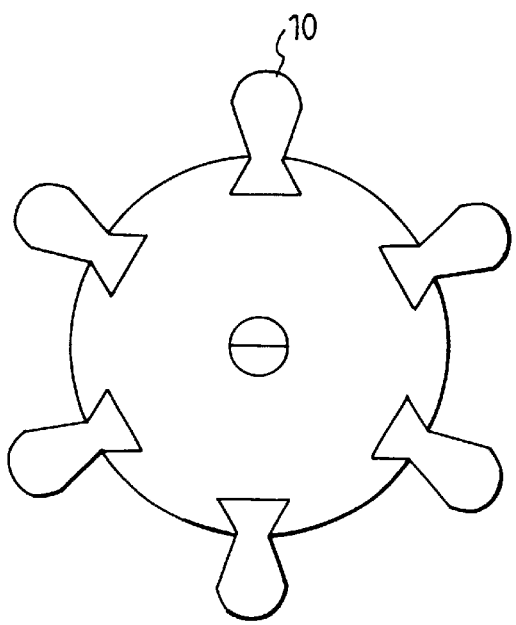
Figure 2C:
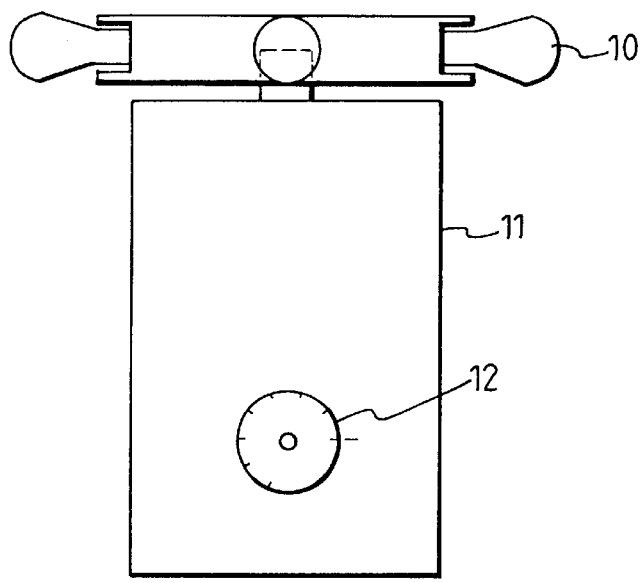

In addition to the global scale transmission, the second type of energy transmission is at the local scale, or through exercise. Again, the resonance is the key issue for the function of the local scale. Referring to FIG. 2, the apparatus implemented in this type can have some extrusions to push a local tissue in a resonant way. FIG. 2A shows the top view of a local resonator with 4 extrusions (10) in order to stimulate the lung meridian into resonance. FIG. 2B is the top view of another local resonator having 6 extrusions (10) in order to stimulate the neck and head into resonance. FIG. 2C shows the side view of a resonator. Inside a housing (11), there are a motor and a transmission mechanism (not shown in the figure). In this embodiment, a fine tuner (12) for the motor speed is placed on a surface of the housing. The stimulation for pushing can also go be done by electricity, while the stimulation is weak. It will move dipole molecules such as lactate and water, but will not cause a twitch of the muscle. It will loosen the blockage in the small artery and reduce impedance. However, stronger stimulation will cause the muscle to twitch and has the same effect as that of exercise. Therefore, the best performance of electrical simulation will be a weak one during the systolic pressure to reduce impedance, and a strong one during the diastolic pressure to produce the effect of synchronized exercise. It should be recognized that these two kinds of stimulation can also be used separately. Since the acupuncture points are the resonant units of the body, the anti-node of the body resonance is a preferable point for delivering the energy at the local scale transmission.

In another embodiment, the apparatus can be in the form of a suction cup and can be used while the suction force is synchronized with the heartbeat. Particularly, the apparatus may be a penis erector or enlarger, breast erector or enlarger, and so on. Since both the penis and breasts are related to the liver meridian, the first harmonic will be its rate while the suction should synchronized with the systolic pressure, which can be monitored by the pressure pulse wave or the R-wave found in an electrocardiogram. The apparatus can be a director for exercise or an exercise machine. When the movement of the limb is synchronized with the heartbeat, it may also generate resonance. Such a mechanism is similar to the intra-aortic balloon and may increase the coronary artery circulation. Actually, the idea of the intra-aortic balloon was derived from a counter pulsation machine, which supplies pressure to the limb during diastolic pressure. Please see the references below:

1. Kantrowitz A., *Experimental augmentation of coronary flow by retardation of the arterial pressure pulse,* Surgery 34, pp.678–687, 1953.
2. O'Rouke M. F., Avolio A. P., Stellion V., *The rhythm of running: Can the heart join in,* Australian and New Zealand J. of the Medicine 23: pp. 708–710, 1993.

For the limb to be synchronized with the heartbeat, the muscle contracts during the diastolic pressure and relaxes during the systolic pressure. Through synchronization, the circulatory system can be improved by at least three ways of: 1.) increasing coronary artery blood flow; 2.) increasing venous return; and 3.) reducing the impedance of the circulation.

Figure 3:
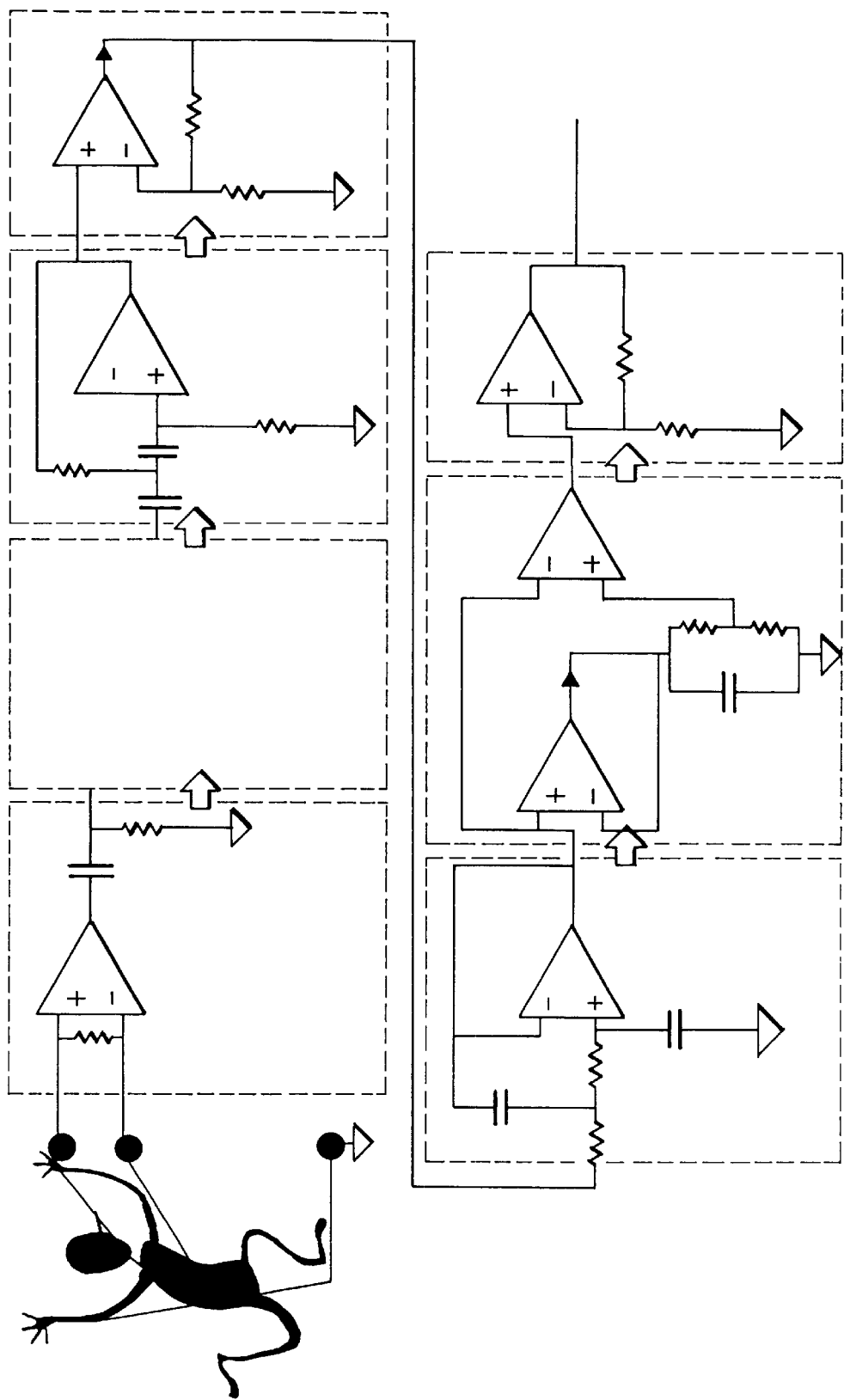
FIG. 3 shows a circuit diagram for detecting R-waves.

A heartbeat monitor is a useful addition to an exercise machine. This can be done by adding an electrocardiogram. FIG. 3 shows a circuit for precise R-wave detection. From the appearance of the R-wave, we can define the time for both the systolic and diastolic wave to arrive at the limbs. The heartbeat must be monitored by the senses such as hearing, seeing and feeling, and must move accordingly. After the R-wave is detected, the signal is used to trigger a sound, a light, or a small signal, such as an electrical signal, to generate the sense to be felt. In general, one movement for each heartbeat following the signals will be helpful. Specifically, legs resonate at the second harmonic of heartbeat, arms resonate at the forth heartbeat, and both head and neck resonate at the sixth harmonic. A large movement is synchronized with the heartbeat, while some fine tuning can be mixed into each movement to enforce the fine resonance figures. The situation is like the meter and beat in music. The rate of heartbeat is the meter, and the resonance harmonics are the beats.

The heartbeat may also be mixed into music to tune the meter and beats. The music will have a meter that is the same as the heart rate, such as 72 beats per minute, while the number of beats in each meter depends on which meridian we try to help. For example, the kidney meridian is at the second harmonic and the music is like a marching song, the spleen meridian is at the third harmonic and the music is like a waltz, and the lung meridian is at the fourth meridian. The instrument playing the music can be a piano, a guitar, etc. The music comes from the instrument played by people or from a player such as a CD or MP-3 player with a tunable meter to synchronize with the heartbeat. Preferably, the meter and beats may also be used to tune the movement of an exercise machine such as a mountain climbing machine, walker, or rowing machine. Also, the meter should be synchronized with the heartbeat, and fine control of the beat should be through the feet (second harmonic), the hands (fourth harmonic) and the head (third or sixth harmonics). The same concept can be applied to the compulsive movement machine for rehabilitation. It is similar to an exercise machine, except that its movement is more restricted by confining the limb or head and etc., and the track of movement may also be defined.

The monitor is essential to the transmitting system and can be used alone to monitor the health conditions of the body, which is disclosed in U.S. Pat. No. 5,730,138, owned by the applicant. For the purpose of monitoring, the theory of normal pattern comparison can be omitted by using the Fourier transformation and by using the standard deviation (S. D.) or coefficient of variance (C. V.) of Ci (i.e. the $i^{th}$ harmonic) or phase to evaluate the improvement of blood circulation, or by using the systolic peak or diastolic minimum as an indication of the heartbeat to monitor the HRV. Usually, HRV is done by EKG.

The electric and mechanical stimulations are described in detail in the pending R.O.C. Patent Application No. 87109823, entitled "Stimulation Apparatus Resonant with Heartbeat," filed on Jun. 17, 1998 by the same inventor as the present invention. The musical player and exercise instruments with a meter and beats are described in detail in the pending R.O.C. Patent Application No. 88107177, entitled "Meter And Beats Apparatus Resonant with Heartbeat," filed on Jun. 7, 1999 by the same inventor as the present invention. The allowed and published R.O.C. Patent Application No. 87116474 (Publication No. 365,529), entitled "Monitoring Method Being Resonant with Heartbeat And Apparatus for Improving Blood Circulation," filed on Oct. 1, 1998 and published on Aug. 1, 1999, relates to the monitoring and mechanical artificial heart.

The step of attaching a pressure sensor on an artery, for measuring the pressure wave formed, can also be replaced by using an electro-optical device, which measures the absorption of a specific wave length on the spectrum. The absorption represents the amount of blood in the artery of a tissue, such as a finger, and the amount of blood in the artery is proportional to the applied pressure (because the artery is made of elastic material). Therefore, from the change of the absorption of a specific wave length of an ingredient such as water or hemoglobin in the blood, the pressure wave formed in the artery can also be monitored.

Monitoring can also be used alone to monitor the deterioration of health conditions while a human is dying. People die mainly under two conditions, one is the death of the heart or lung, and the other is brain death. These two conditions can be monitored by the fourth harmonic indicator of the heartbeat indicating the lung meridian, and the sixth harmonic indicator indicating the gall-bladder meridian, which supplies blood toward the head. However, for the death of the brain stem, the indicator is of the first harmonic indicating the liver meridian. When the C. V. of these indicators gets larger, it implies the patient is closer to death. When a certain limit is exceeded, the condition becomes fatal and intensive care must be provided.

The death of rats, and of human beings, has been monitored. When the C. V. is at the fourth harmonic which exceeds a certain limit, for example 100%, the chance of death becomes very high. When the first harmonic C. V. is over 10%, or the phase becomes faster, it can be an indicator of brain stem death.

While monitoring the function of an energy transmitting device, a simple monitoring concept is when the C. V. increases and the intensity becomes lower, the condition of dying for lack of blood supply is implied. Thus the transmitting efficiency can be monitored by: 1.) the reduction of C. V. values; 2.) the increasing of the intensity of a specific harmonic, except for the C1, the first harmonic (where the increasing of C1 could be due to poisoning); and 3.) the increasing of the HRV. In fact, the monitoring factors can be generally used in any treatment, such as drug, physical therapy, specially designed exercise, or they can be used for monitoring at an ICU or as a bed-side monitor.

From the invention thus described, it will be obvious that the embodiments and description are not intended to limit the invention. The invention may be varied in many ways. Such variations are not to be regarded as a departure from the spirit and scope of the invention, and all such modifications, as would be obvious to one skilled in the art, are intended for inclusion within the scope of the following, claims.

What is claimed is:

1. A method for improving blood circulation of a human body by resonance, comprising the steps of:

(a) using an energy generating device to generate energy with a period synchronizing with the heartbeat of the body; and (b) coupling the energy through a coupling device to the circulatory system of the body by functionally connecting the coupling device to the body and then activating the energy generating device.

2. The method as claimed in claim 1, wherein the energy generating device is an artificial heart and step (b) further comprises connecting tubes to an artery of the body.

3. The method as claimed in claim 1, wherein the energy generating device comprises a motor with a speed synchronized with the heartbeat of the body.

4. The method as claimed in claim 3, wherein the step (b) further comprises:

(c) providing an impedance matched mattress filled with excited fluid;

(d) exciting the natural frequency of the mattress by the motor; and (e) treatment by subjecting the body to the mattress.

5. The method as claimed in claim 3, wherein the heartbeat is measured by an EKG.

6. The method as claimed in claim 3, wherein the coupling device comprises a cup to be fitted into an extrusive part of the body, and the energy generating device comprises a suction pump to be turned on to suck on the extrusive part.

7. The method as claimed in claim 3, wherein the coupling device comprises a disk with a number of extrusive parts. The disk is driven by a motor to rotate at a rate identical to the rate of the heartbeat which is selected according to the designated meridian for application.

8. The method as claimed in claim 3, the coupling channel comprises an exercise machine moving with the rate of the heartbeat as meter and may be fine-tuned according to the beat requirement of the limbs.

9. The method as claimed in claim 1, wherein said energy generating device comprises a music playing machine, and said coupling device comprises a dancing or exercising machine.

10. The method as claimed in claim 1, wherein said energy generated by said energy generating device is in the form of one selected from the group of sound, light, electricity and pressure, and said coupling device comprises either a sensor organ or an artificial sensor device.

11. A method for improving blood circulation of a human body by resonance, comprising the steps of:
   (a) using an energy generating device to generate energy resonating with the body;
   (b) coupling the energy through a coupling device to the circulatory system of the body by functionally connecting the coupling device to the body and then activating the energy generating device; and
   (c) further comprising the step of feedback-control of the energy generating device by a monitoring device.

12. The method as claimed in claim 11, wherein the monitoring device comprises a pulse analysis machine to analyze the pulse spectrum of the body.

13. The method as claimed in claim 11, wherein the monitoring device comprises a heart rate variation machine to analyze the HRV of the body.

14. The method as claimed in claim 11, further comprising the following steps performed by the monitoring device:
   (a) measuring pressure waves formed in an artery of the body and producing an electrical pulse representing a blood pressure pulse; and
   (b) calculating the amplitude and the phase of harmonic components of the electrical pulse by applying Fourier transformation theory to the harmonics of the electrical pulse.

15. The method as claimed in claim 14, wherein the step of measuring the pressure wave comprises the step of sensing the blood pressure pulse in an artery of the body with a pressure transducer.

16. The method as claimed in claim 14, wherein the step of measuring the pressure waves comprises directing a light beam toward the blood in the artery and then measuring absorption rate of a blood component by a photo detector.

17. The method as claimed in claim 16, wherein the blood component comprises water.

18. The method as claimed in claim 16, wherein the blood component comprises hemoglobin.

19. The method as claimed in claim 14, wherein the step (b) further comprises displaying a standard deviation of the measured harmonic component.

20. The method as claimed in claim 19, wherein the step (b) further comprises using a coefficient of variance, which equals a standard deviation divided by the mean, as an indicator.

21. The method as claimed in claim 14, wherein the fourth harmonic is used to monitor the health condition of the lung and lung meridian of the body.

22. The method as claimed in claim 14, wherein the sixth harmonic is used to monitor the health condition of the gall-bladder meridian of the body.

23. The method as claimed in claim 14, wherein the first harmonic is used to monitor the health condition of the liver meridian which includes the brain stem.

24. An apparatus for improving the blood circulation of a human body by resonance comprising an energy generating device for generating an energy with a period synchronizing with the heartbeat of the body, and coupling device for delivering the energy to the circulatory system of the body.

25. The apparatus as claimed in claim 24, wherein the energy generating device comprises a motor rotating at a rate identical to that of the heart rate, and the coupling device comprises a disk attached to a motor with a number of extrusive parts.

26. The apparatus as claimed in claim 25, wherein the number of extrusive parts is selected according to the meridian to be treated.

27. The apparatus as claimed in claim 24, the energy generating device comprises a heartbeat detector.

28. The apparatus as claimed in claim 24, the energy generating device comprises an electrical signal generator and a coupling device is functionally connected to a part of the body.

29. The apparatus as claimed in claim 28, the electrical signal comprises a weak stimulus which is delivered during the appearance of systolic pressure in the body and will cause a muscular twitch.

30. The apparatus as claimed in claim 28, the electrical signal comprises a strong stimulus which is delivered during the appearance of diastolic pressure in the body and will not cause any muscular twitch.

31. The apparatus as claimed in claim 24, wherein the coupling device is further coupled to an acupuncture point.

32. The apparatus as claimed in claim 24, wherein the energy generating device comprises a suction pump, and the coupling device comprises a cup for fitting onto an extrusive part of the body.

33. The apparatus as claimed in claim 32, wherein the extrusive part of the body comprises the penis of the body.

34. The apparatus as claimed in claim 32, wherein the extrusive part of the body comprises the breast of the body.

35. The apparatus as claimed in claim 24, wherein said energy generating device comprises a measuring instrument with a controllable meter to be synchronized with the heartbeat of the body, and said coupling device comprises a dancing of exercising machine.

36. An apparatus for improving the blood circulation of a human body by resonance comprising an energy generating device for generating an energy resonant with the body, and coupling device for delivering the energy to the circulatory system of the body, wherein the coupling device further comprises a mattress filled with fluid and a frequency tuning device and the energy generating device further comprises a motor driven device for sending energy to the mattress so as to generate resonant waves in the mattress.

37. The apparatus as claimed in claim 36, wherein the frequency tuning device further comprises a pressure controlling device.

38. The apparatus as claimed in claim 36, wherein the frequency tuning device further comprises a shape changing device.

* * * * *